ically substituted benzoic acids have been patented.

United States Patent

Hanselmann

[11] Patent Number: 5,486,622
[45] Date of Patent: Jan. 23, 1996

[54] PROCESS AND INTERMEDIATE PRODUCTS FOR THE PRODUCTION OF 5-OXASPIRO [2.4] HEPTAN-6-ONE

[75] Inventor: Paul Hanselmann, Visp, Switzerland

[73] Assignee: Lonza Ltd., Gampel/Valais, Switzerland

[21] Appl. No.: 417,250

[22] Filed: Apr. 5, 1995

[30] Foreign Application Priority Data

Apr. 21, 1994 [CH] Switzerland .............................. 1230/94

[51] Int. Cl.⁶ ...................... C07D 307/94; C07D 307/26; C07C 255/00
[52] U.S. Cl. ........................... 549/265; 549/323; 549/324; 549/510; 558/384; 558/451
[58] Field of Search ..................................... 549/265, 324, 549/510, 323; 558/451, 384

[56]  References Cited

FOREIGN PATENT DOCUMENTS

0480717A1   4/1992   European Pat. Off. .

OTHER PUBLICATIONS

F. Govaert and P. Cornand, Meded. K. Vlaam, Acad. Wet., Lett. Schone Kunsten Belg., Kl. Wet., (16), (1954), 1–13.
D. Wendisch, Methoden Org. Chem. [Methods of Org. Chem.] (Houben–Weyl), 4th Edition, vol. IV/3, pp. 32–42.

*Primary Examiner*—C. Warren Ivy
*Assistant Examiner*—Amelia Owens
*Attorney, Agent, or Firm*—Fisher, Christen & Sabol

[57]  ABSTRACT

5-Oxaspiro[2.4]heptan-6-one:

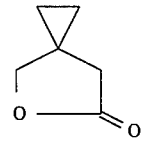

I is obtained from [3-(hydroxymethyl)oxetan-3-yl]acetonitrile by reaction with hydrogen bromide and then cyclizing the intermediate product 4,4-bis(bromomethyl)dihydro-2-furanone with zinc. 5-Oxaspiro[2.4]heptan-6-one is an intermediate product for the production of leukotriene antagonists.

8 Claims, No Drawings

PROCESS AND INTERMEDIATE PRODUCTS FOR THE PRODUCTION OF 5-OXASPIRO [2.4] HEPTAN-6-ONE

BACKGROUND OF THE INVENTION

1. Field of the Invention

The invention relates to a new process for the production of 5-oxaspiro[2.4]heptan-6-one of formula:

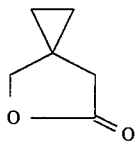
I as well as new intermediate products of the process according to the invention.

2. Background Art

5-Oxaspiro[2.4]hepzan-6-one (I) is an intermediate product for the production of leukotriene antagonists (European Published Patent Application No. 0480717). A known synthesis of compound (I) starts from itaconic acid ester and ends with the reduction of the cyclic anhydride 5-oxaspiro [2.4]heptane-4,6-dione to compound of formula (I). But this reduction yields a mixture of the desired product wit the isomeric 5-oxaspiro[2.4]heptan-4-one and is, therefore, less than suitable for the reasonably-priced production of large amounts of the desired product.

BROAD DESCRIPTION OF THE INVENTION

The main object of the invention is to provide a process for the production of 5-oxaspiro[2.4]heptan-6-one, which starts from easily accessible materials and does not require any separation of isomers. Other objects and advantages of the invention are set out herein or are obvious herefrom to one skilled in the art.

The objects and advantages of the invention are achieved by the process and intermediates of the invention.

The invention involves a process for the production of 5-oxaspiro[2.4]heptan-6-one of the formula:

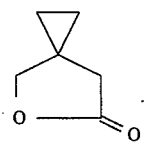
I

[3-Hydroxymethyl)oxetan-3-yl]acetonitrile of the formula:

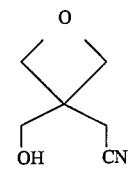
II is converted with hydrogen bromide to 4,4-bis(bromomethyl)dihydro-2-furanone of the formula:

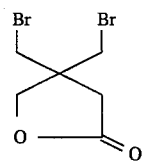
III and the latter is cyclized with zinc to the compound of formula I.

Preferably the conversion of the nitrile (II) to the bis(bromomethyl) compound (III) by the 3,3-bis(hydroxymethyl)-4-bromobutyronitrile of the formula:

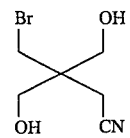
IV and/or the 4-(bromomethyl)-4-(hydroxymethyl)dihydro-2-furanone of the formula:

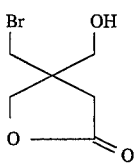
V is performed in two or three stages. Also preferably the conversion of the nitrile (II) to the bis(bromomethyl) compound (III) is performed in one stage with excess hydrogen bromide. Preferably the conversion reaction is performed with hydrogen bromide in acetic acid or a polar aprotic solvent and/or water.

The invention also involves: 4,4-bis(bromomethyl)dihydro-2-furanone of the formula:

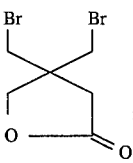
III 3,3-bis(hydroxymethyl)-4-bromobutyronitrile of the formula:

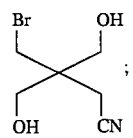
IV and 4-(bromomethyl)-4-(hydroxymethyl)dihydro-2-furanone of the formula:

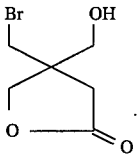
V

DETAILED DESCRIPTION OF THE INVENTION

It has been found that the [3-(bromomethyl)-oxetan-3-yl] acetonitrile of the formula:

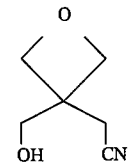
II which is easily accessible from pentaerythritol dibromide (F. Govaert and P. Cornand, Meded. K. Vlaam. Acad. Wet., Lett. Schone Kunsten Belg., Kl Wet., (16), (1954), 1–13), can be converted in a simple way by treatment with hydrogen bromide to 4,4-bis(bromomethyl)dihydro-2-furanone of the formula:

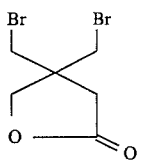

The bis(bromomethyl) compound (III) can then be cyclized to the compound of formula I in a good yield by treatment with zinc.

The conversion of the nitrile (II) to the bis(bromomethyl) compound (III) occurs in a varying manner depending on reaction conditions, so that either isolatable intermediate products result, which are to be converted to the bis(bromomethyl) compound (III) in one or two additional stages by further action of hydrogen bromide, or the bis(bromomethyl) compound (II) is obtained directly in a single stage. In this case, the wording "in a single stage" relates only to the practical implementation of the synthesis and does not mean that the reaction actually occurs in one step.

With use of a little hydrogen bromide, for example, about 1 mol of HBr on 1 mol of the nitrile (II), and relatively mild conditions (room temperature), the 3,3-bis(hydroxymethyl)-4-bromobutyronitrile of the formula:

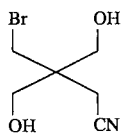

is obtained as a first isolatable product. In somewhat more rigorous reaction conditions, for example, 80° C. and about 2 mol of HBr on 1 mol of the nitrile (II), the 4-(bromomethyl)-4-(hydroxymethyl)-dihydro-2-furanone of the formula:

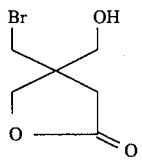

results as isolatable product. Both the bis(hydroxy-methyl)nitrile (IV) and the bromomethyl-hydroxymethyl-lactone (V) can be converted to bis(Dromomethyl) compound (III) by further reaction with hydrogen bromide. But for this purpose, more drastic reaction conditions (for example, 120° C., 10 equivalents of HBr) are necessary.

If nitrile (II) is treated with an excess of hydrogen bromide, i.e., with more than 3 mol of HBr on 1 mol of the nitrile (II), then the conversion to the bis(bromomethyl) compound (III) is possible in one stage.

As solvents, in which the reaction of the nitrile (II) or the further reaction of the bis(hydroxymethyl)nitrile (IV) or the bromomethyl-hydroxymethyl-lactone (V) can be performed with hydrogen bromide, for example, polar aprotic solvents, such as N,N-dimethylformamide or N,N-dimethylacetamide, protic solvents, such as low carboxylic acids or water, as well as mixtures of these solvents are suitable. Especially preferred are acetic acid, polar aprotic solvents by themselves or in a mixture with water or water by itself.

The hydrogen bromide can be added or fed in the reaction mixture both as a commercially available solution in water or acetic acid and in a gaseous state.

The cyclization of the bis(bromomethyl) compound (III) to the 5-oxaspiro[2.4]heptan-6-one (I) with zinc like an intramolecular Wurtz synthesis can take place analogously to known syntheses of other compounds with a cyclopropane ring from the corresponding 1,3-dihalogen compounds. A survey on this type of reaction is found, for example, in D. Wendisch, Methoden Org. Chem. [Methods of Org. Chem.] (Houben-Weyl), 4th Edition, Vol. IV/3, pp. 32–42. As solvent, especially low alcohols, such as, ethanol or amides, such as, N,N-dimethylacetamide, are suitable.

In the working-up, care must suitably be taken that strongly basic or nucleophilic conditions are avoided, since otherwise the lactone ring can be opened. This is possible especially in the presence of alcohols, in which the corresponding hydroxyesters are formed.

The following examples illustrate the implementation of the process according to the invention.

EXAMPLE 1

[3-(Bromomethyl)oxetan-3-yl]methanol

A solution of 25 g (94 mmol) of 2,2-bis(bromomethyl)-1,3-propanediol (pentaerythritol dibromide) in 250 ml of ethanol was stirred with 6.1 g (94 mmol) of potassium hydroxide (86 percent, pellets) for 2 hours at room temperature. Then, the potassium bromide that had developed, was filtered off and the filtrate was concentrated by evaporation in a vacuum. The thus-obtained yellowish oil was usable for the following stage without further purification. The yield (crude product) was 18.1 g (100 percent). The boiling point of the product was 86° C./0.2 torr Other data concerning the product was:

$^1$H-NMR (CDCl$_3$, 300 MHz): δ4.49, 4.47 (AB system, $J_{AB}$=7.5 Hz, 4 H, ring-H); 3.96 (s, 2 H, CH$_2$OH); 3.78 (s, 2 H, CH$_2$Br); 3.50 (s, 1 H, OH).

EXAMPLE 2

[3-(Hydroxymethyl)-oxetan-3-yl]acetonitrile (II)

A solution of 42 g (0.23 mol) of [3-(bromomethyl)oxetan-3-yl] methanol (produced according to Example 1) in 420 ml of ethanol was refluxed with 13 g (0.265 mol) of sodium cyanide for 18 hours. After cooling to room temperature, the precipitated sodium bromide was filtered off and the filtrate concentrated by evaporation. The residue was distilled at 0.4 torr. The yield of product as a colorless oil was 16 g (54 percent). The boiling point of the product was 107° C./0.4 torr. Other data concerning the product was:

$^1$H-NMR (CDCl$_3$, 300 MHz): δ4.43 (s, 4 H, ring-H); 3.97 (s, 2 H, CH$_2$OH); 2.85 (s, 2 H, CH$_2$CN); 2.50 (s, 1 H, OH).

IR(Film): ν=2247 cm$^{-1}$ (C≡N)

EXAMPLE 3

3,3-Bis(hydroxymethyl)-4-bromobutyronitrile (IV)

A mixture of 176 mg (1.39 mmol) of [3-(hydroxymethyl)oxetan-3-yl]acetonitrile (II, produced according to Example 2) and 2.5 ml of N,N-dimethylacetamide was mixed at 10° C. with 289 mg of aqueous hydrobromic acid (48 percent HBr). After the flattening-out of the exothermic reaction, the mixture was poured on ice and then extracted with diethyl ether. By concentration by evaporation of the ethel" phase, a crude product was obtained, which still contained some N,N-dimethylacetamide. The yield was 440 mg of crude product, according to 1H-NMR integration 64 percent of theory. Other data concerning the product was:

$^1$H-NMR (CDCl$_3$, 300 MHz): δ3.95 (s, 2 H, OH); 3.67 (s, 4 H, CH$_2$OH); 3.54 (s, 2 H, CH$_2$Br); 2.59 (s, 2 H, CH$_2$CN).

IR(Film): ν=2244 cm$^{-1}$ (C≡N)

EXAMPLE 4

4-(Bromomethyl)-4-(hydroxymethyl)dihydro-2-furanone (V)

A mixture of 1.76 g (13.9 mmol) of [3-(hydroxymethyl)oxetan3-yl]acetonitrile (II, produced according to Example 2) and 5 ml of N,N-dimethylacetamide was mixed at room temperature with 4.85 g of aqueous hydrobromic acid (48 percent HBr) and, after the flattening-out of the exothermic reaction, heated for 2 more hours to 90° C. Then, the reaction mixture was poured on ice and extracted with ethyl acetate. By concentration by evaporation of the organic phase, a crude product was obtained, which still contained some N,N-dimethylacetamide. The yield was 1.45 g of crude product, according to 1H-NMR integration 39 percent of theory. Other data concerning the product was:

$^1$H-NMR (CDCl$_3$, 400 MHz): δ4.28, 4.21 (AB system, J$_{AB}$=10 Hz, 2 H, ring CH$_2$O); 3.77 (s, 2 H, CH$_2$OH); 3.58 (s, 2 H, CH$_2$Br); 2.68 (s, 1 H, OH); 2.63, 2.56 (AB system, J$_{AB}$=16 Hz, 2 H, CH$_2$C=O).

IR(Film): v=1776 cm$^-$(C=O)

EXAMPLE 5

4,4-Bis (bromomethyl)dihydro-2-furanone (III)

A mixture of 29 g (138 mmol) of 4-(bromomethyl-4-(hydroxymethyl)-dihydro-2 -furanone (V, produced according to Example 4) and 69 g of aqueous hydrobromic acid (48 percent HBr) was heated for 5 hours to 120° C. Then, the reaction mixture was poured on ice and extracted with diethyl ether. During concentration by evaporation of the ether, the product crystallized out. The yield of product was 23.7 g (63 percent). The melting point of the product was 72° C. (H$_2$O). Other data concerning the product was:

$^1$H-NMR (CDCl$_3$ 300 MHz): δ4.28 (S, 2 H, CH$_2$O); 3.68 (s, 4 H, CH$_2$Br); 2.72 (s, 2 H, CH$_2$C=O).

IR(KBr): v=1786 cm$^-$(C=O)

EXAMPLE 6

4,4-Bis(bromomethyl)dihydro-2-furanone (I. II, one-stage variant)

At room temperature, 1.0 g (7.3 mmol) of [3-(hydroxymethyl)oxetan-3-yl] acetonitrile (II, produced according to Example 2) was mixed with 8.93 g (36.6 mmol) of hydrogen bromide (30 percent solution in acetic acid). After the flattening-out of the strongly exothermic reaction, the mixture was also heated for 1 more hour to 100° C. After cooling to room temperature, the precipitated salt (ammonium bromide) was filtered off, and the filtrate evaporated to dryness at 50° C./10 mbars. The residue was taken up in water/diethyl ether and neutralized with saturated sodium bicarbonate solution. After separating the organic phase, the aqueous phase was extracted three more times with diethyl ether. The combined organic phases were dried with sodium sulfate and concentrated by evaporation. 1.85 g of a white solid with a content (after GC)>90 percent remained.

EXAMPLE 7

5-Oxaspiro[2.4]heptan-6-one (I)

0.2 g (0.73 mmol) of 4,4-bis-(bromomethyl)dihydro-2-furanone (III, produced according to Example 5) and 80 mg (1.2 mmol) of zinc powder were introduced in 2.5 ml of N,N-dimethylacetamide at room temperature and heated for 5 hours to 120° C. The reaction mixture was then poured on ice and extracted with ethyl acetate. By concentration by evaporation of the organic phase, 80 mg of crude product was obtained, which still contained some N,N-dimethylacetamide according to GC-MS. Other data concerning the product was:

$^1$H-NMR (CDCl$_3$, 300 MHz): δ4.19 (s, 2 H, CH$_2$O); 2.56 (s, 2 H, CH$_2$C=O); 0.70–0.78 (m, 4 H, three-membered ring-H).

IR(Film): v=1777 cm$^-$(C=O)

EXAMPLE 8

5-Oxaspiro[2.4]heptan-6-one (I)

2.0 g (6.6 mmol) of 4,4-bis-(bromomethyl)dihydro-2-furanone (III, produced according to Example 5) and 0.89 g (13.2 mmol) of zinc powder were introduced in 20 ml of N,N-dimethylacetamide at room temperature and heated for 2 hours to 120° C. After cooling to room temperature, 2.4 g of ammonia gas was introduced, and the formed precipitate as well as the zinc powder (total 2.35 g) were filtered off. The filtrate was concentrated by evaporation at 70°–80° C./15 mbars. 1.25 g of a yellowish liquid remained, which after GC consisted of 53 percent of N,N-dimethylacetamide and 46 percent of lactone. For final purification, the crude product was taken up in diethyl ether/water and yielded the spirolactone of formula I (88 mg) after working-up and bulb tube distillation.

What is claimed is:

1. A process for the production of 5-oxaspiro[2.4]heptan-6-one of formula:

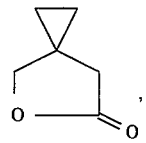   I comprising converting [3-(hydroxymethyl)oxetan-3-yl]acetonitrile of formula:

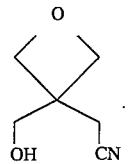   II with hydrogen bromide to 4,4-bis(bromomethyl)dihydro-2-furanone of formula:

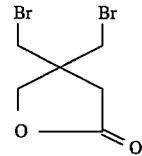   III and cyclizing the 4,4-bis(bromoethyl)dihydro-2-furanone of formula III with zinc to the 5-oxaspiro[2.4]heptan-6-one of formula I.

2. The process according to claim 1 wherein the conversion of the [3-(hydromethyl)oxetan-3-yl]acetonitrile to the 4,4-bis(bromoethyl)dihydro-2-furanone of formula II by 3,3-bis(hydroxymethyl)-4-bromobutyronitrile of formula:

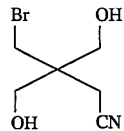   IV and/or the 4-(bromomethyl)-4-(hydroxymethyl)dihydro-2-furanone of formula:

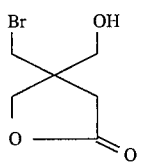

is performed in two or three stages.

3. The process according to claim 1 wherein the conversion of the [3-(hydromethyl)oxetan-3-yl]acetonitrile to the 4,4-bis(bromoethyl)dihydro-2-furanone of formula III is performed in one stage with excess hydrogen bromide.

4. The process according to claim 3 wherein the reaction is performed with hydrogen bromide in acetic acid or a polar aprotic solvent and/or water.

5. The process according to claim 1 wherein the reaction is performed with hydrogen bromide in acetic acid or a polar aprotic solvent and/or water.

6. 4,4-Bis(bromomethyl)dihydro-2-furanone of formula:

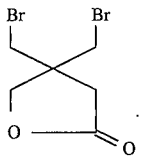

7. 3,3-Bis(hydroxymethyl)-4-bromobutyronitrile of formula:

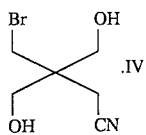

8. 4-(Bromomethyl)-4-(hydroxymethyl)dihydro-2-furanone of formula:

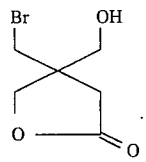

* * * * *